(12) United States Patent
Yin (10) Patent No.: US 8,416,102 B2
(45) Date of Patent: Apr. 9, 2013

(54) ACTIVITY MONITORING SYSTEM INSENSITIVE TO ACCELERATIONS INDUCED BY EXTERNAL MOTION FACTORS

(75) Inventor: Bin Yin, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 12/919,778

(22) PCT Filed: Mar. 5, 2009

(86) PCT No.: PCT/IB2009/050896
§ 371 (c)(1),
(2), (4) Date: Aug. 27, 2010

(87) PCT Pub. No.: WO2009/112981
PCT Pub. Date: Sep. 17, 2009

(65) Prior Publication Data
US 2011/0012759 A1    Jan. 20, 2011

(30) Foreign Application Priority Data
Mar. 14, 2008 (EP) .................................... 08152746

(51) Int. Cl.
H03K 17/94 (2006.01)
(52) U.S. Cl. ......................................................... 341/20
(58) Field of Classification Search .................... 341/20; 600/587, 595
See application file for complete search history.

(56) References Cited

U.S. PATENT DOCUMENTS

| | | | |
|---|---|---|---|
| 6,166,644 A * | 12/2000 | Stroda ........................... | 600/595 |
| 6,280,409 B1 | 8/2001 | Stone et al. | |
| 6,436,052 B1 | 8/2002 | Nikolic et al. | |
| 7,918,801 B2 * | 4/2011 | Cochran ........................ | 600/587 |
| 8,206,325 B1 * | 6/2012 | Najafi et al. .................... | 600/595 |
| 2002/0116080 A1 | 8/2002 | Birnbach et al. | |
| 2007/0167879 A1 * | 7/2007 | Cochran ........................ | 600/595 |

FOREIGN PATENT DOCUMENTS
WO    2004052202 A1    6/2004

OTHER PUBLICATIONS

David Mizell: "Using Gravity to Estimate Accelerometer Orientation", Wearable Computers, 2003, Proc. 7th IEEE Intnl Symposiumon, Oct. 21-23, 2003, Piscataway, NJ, pp. 252-253, XP010673894.

P.H. Veltink et al: "Detection of Static and Dynamic Activities Using Uniaxial Accelerometers", IEEE Trans on Neural Systems and Rehabilitation, vol. 4, Dec. 4, 2006.

* cited by examiner

Primary Examiner — Khanh V Nguyen (57) ABSTRACT

This invention relates to an activity monitoring system adapted to eliminate passive movement components caused by external forces from readout data produced by a first and a second motion sensor when attached to a subject during movement. The readout data include gravitational components, movement components caused by active movement of the subject or subject parts, and the passive movement components. A processor estimates first and second gravitational components produced by the at least first and a second motion sensors. It determines a rotation matrix based on the estimated gravitational components, the rotation matrix denoting rotation required for the first sensor to get aligned with the second sensor in orientation. It then multiplies the readout data produced by the first motion sensor with the rotation matrix when rotating the first sensor towards the second sensor. Finally, it subtracts the result of the multiplying from the readout data produced by the second motion sensor when rotating the first motion sensor towards the second motion sensor.

12 Claims, 6 Drawing Sheets

ACTIVITY MONITORING SYSTEM INSENSITIVE TO ACCELERATIONS INDUCED BY EXTERNAL MOTION FACTORS

FIELD OF THE INVENTION

The present invention relates to an activity monitoring system and a method adapted to process readout data produced by at least a first and a second motion sensors when attached to a subject during movement, the readout data including, for each respective motion sensor, a gravitational component, a movement component caused by active movement of the subject or subject parts, and a passive movement component caused by external forces, where processing the data results in that the passive movement components get eliminated.

BACKGROUND OF THE INVENTION

Accelerometry-based activity monitoring systems are getting more and more widely used. The applications spread over medical and healthcare, rehabilitation, pharmacology and consumer lifestyle domains. For instance, in patient monitoring, the activity sensor provides contextual information that helps to improve the evaluation accuracy of patients' vital body signs, such as ECG and EMG signals; in consumer lifestyle domain, an activity monitor (AM) enables the estimation of energy expenditure (EE) associated with physical activities (PAs) as well as the identification and classification of PAs. Compared to other methods such as video recording, electromyography and questionnaires, accelerometry provides a tool suitable for objective, reliable, long term and low cost monitoring of free-living subjects, with very limited restrictions on their daily lives.

An AM system typically consists of a (number of) triaxial accelerometer(s) and a data logging unit. Sometimes gyroscopes and/or magnetometers are also present. When an accelerometer stays still, it measures the earth gravity g that is decomposed along its three sensing axes. The readout vector can be denoted as $$V_g = (x_g, y_g, z_g). \quad (1)$$

If the accelerometer starts to move, besides gravitational acceleration, also inertial acceleration is recorded that results from the movement. Movement of the sensor can be caused by the active movement of the body part to which the sensor is attached as well as the "passive" movement due to external forces. Passive movements can occur, for example, when traveling in a vehicle, cycling on a bumpy road or working with a mowing machine. The readout $V_a$ of a moving accelerometer can be therefore described as:

$$V_a = V_g + V_{act} + V_{pas},$$

$$V_{act} = (x_{act}, y_{act}, z_{act}),$$

$$V_{pas} = (x_{pas}, y_{pas}, z_{pas}), \quad (2)$$

where $V_{act}$ denotes the acceleration from the active movement, and $V_{pas}$ the acceleration from the passive movement.

The presence of $V_g$ has been proven to have no significant impact on the accuracy of predicting activity related EE (AEE) [1], but apparently the external motion factors induced acceleration $V_{pas}$ should not be taken into account. Unlike $V_g$ that is in general the DC of the signal $V_a$ and may be quite well estimated simply by low-pass filtering $V_a$, $V_{pas}$ is often mixed up with $V_{act}$ in time domain usually as well as in frequency domain, so direct filtering does not always work.

In some special cases, the contribution of $V_{act}$ to $V_a$ is negligible. For instance, when the subject is sitting in or driving a car, a waist-mounted accelerometer measures mostly the acceleration generated by the car, which can come from the road roughness, the motor vibration and/or the speed change, and $V_{act}$ is almost zero in this case. Thus, if the activity can be correctly recognized as driving, then the acceleration data corresponding to this activity may be excluded from the AEE calculation.

In WO2004/052202A1, a user interface was proposed for an activity monitor that allowed the input from the user indicating the occurrence of "fake" events, such as driving, where the device mainly records external motions, so that a correction factor can be applied in AEE calculation. Also, an automatic scheme based on a single- or multiple-sensor system was described where those events could be recognized by an activity classification algorithm using the readout of the sensor(s). In U.S. Pat. No. 6,280,409B1 and US2002/0116080A1, similarly, a set of thresholding methods was introduced. With these methods, in the former case, the undesired impact of driving on the assessment of the level of activities of daily living (ADL) was largely reduced, and in the latter case, false alarms were avoided in an accelerometry-based system that was capable of judging whether a person would need assistance by monitoring his/her movement changes and could be falsely triggered when he/she was traveling in a vehicle.

There are some obvious drawbacks in the abovementioned methods. Manual fake event indicator requires user intervention, which in practice may lead to inconveniences as well as inaccurate duration information of the events. The reliability of automatic activity recognition methods (of which thresholding methods are a subset) still remain questionable in terms of their robustness over various users and under non-laboratory environments, even though they show acceptable performances on test data sets usually of limited size. More importantly, a common shortcoming is that these methods work only in the case where $V_{act} \approx 0$ and $V_{pas}$ is dominant, such as traveling in a vehicle. They are not able to tackle situations in which $V_{act}$ and $V_{pas}$ are comparable in magnitude or $V_{pas}$ has a non-negligible effect though $V_{act}$ is dominant. A typical example would be cycling on a very rough road.

BRIEF DESCRIPTION OF THE INVENTION

The object of the present invention is to overcome the above mentioned drawbacks by providing a system and a method that eliminates acceleration signals caused by passive movements and remains the true activity induced acceleration signals.

According to one aspect the present invention relates to an activity monitoring system adapted to eliminate passive movement components caused by external forces from readout data produced by at least a first and a second motion sensor when attached to a subject during movement, the readout data including gravitational components, movement components caused by active movement of the subject or subject parts, and the passive movement components, the system comprising:

a processor adapted to:
estimating a first and second gravitational components produced by the at least first and a second motion sensors,
determining a rotation matrix based on the estimated gravitational components, the rotation matrix denoting rotation required for the first sensor to get aligned with the second sensor in orientation, multiplying the readout data produced by the first motion sensor with the rotation matrix when rotating a first sensor towards a second sensor, and subtracting the result of the multiplying from the readout data produced by the second motion sensor when rotating the first motion sensor towards the second motion sensor.

Accordingly, by processing the readouts from the two or more motion sensors, the readout data caused by the passive movements can be cancelled out, i.e. the system becomes independent of the passive movement components but remains the true activity induced acceleration signals. This results in that the problem of being sensitivity to external motion factors, which is e.g. intrinsic for accelerometry-based PA assessment systems, gets solved. The reliability of the system will thus increase enormously because it becomes robust against all types of environments, e.g. where the active movement components $V_{act}$ and the passive movement components $V_{pas}$ are comparable in magnitude, or where $V_{pas}$ has a non-negligible effect though $V_{act}$ is dominant such as cycling on a very rough road.

In one embodiment, the motion sensors are attached to the subject at respective positions such that the orientation of the motion sensors coordinate system changes differently when the subject experiences a motion. In one embodiment, the respective positions are different body parts of the subject.

Thus, the sensors may be attached to for example waist, chest, arm, wrist, thigh and ankle. The proposed solution requires that the sensors should be placed on the body parts that generate significantly different acceleration signals. This will be discussed in more details later.

In one embodiment, the motion sensors are three or more motion sensors. They can form two or more motion sensor pairs by either grouping each two sensors or selecting one sensor and grouping the rest with this sensor respectively, the steps of eliminating the passive movement components being performed for each respective motion sensor pair.

Accordingly, multiple readouts are provided which can process in various ways, e.g. by taking the average value from the sensor pairs as a final readout value.

In one embodiment, the motion sensors are three or more motion sensors forming two or more motion sensor pairs, the processing further including selecting one motion sensor pair from the two or more motion sensor pairs as the first and the second motion sensor, the selection being based on monitoring which readout data differ most from the three or more motion sensors.

Accordingly, the larger the difference is in the readout data the more unlikely it is that the final processed readout will approach zero. Also, the result will be that the measurement becomes more stable and accurate.

In one embodiment, the motion sensors are tri-axial accelerometers.

In one embodiment, the motion sensors are integrated into the system and form a hand-held device.

Accordingly, a hand-held system is provided where the processor may be integrated to a PDA, mobile telephone, watch, etc.

In one embodiment, the system further comprising a receiver adapted to be coupled to the processor, the motion sensors being externally located and adapted to transmit the readout data to the receiver.

Thus, the processing may take place by an external computer system, which makes the system more economical for the subject. As an example, an external computer system could be provided at a health care provider where all the processing steps take place. Thus, only the motions sensors need to be carried by the subject.

In one embodiment, the system further comprises a memory for storing the readout data produced by at least a first and a second motion sensor.

Thus, the at least first and the second motion sensor may form a sensor unit assembly that is separate from the processor. Therefore, the readout data can e.g. later get uploaded to an external computer where data above mentioned processing takes place.

According to another aspect, the present invention relates to an activity monitoring kit comprising:

a processor, and at least a first and a second motion sensor adapted to be coupled to the processor, the processor being adapted to eliminating passive movement components caused by external forces from the readout data produced by the motion sensors when attached to a subject during movement, the readout data including gravitational components, movement components caused by active movement of the subject or subject parts, and the passive movement components, the eliminating of the passive movement components comprising:

estimating a first and second gravitational components produced by the at least first and a second motion sensors, determining a rotation matrix based on the estimated gravitational components, the rotation matrix denoting rotation required for the first sensor to get aligned with the second sensor in orientation, multiplying the readout data produced by the first motion sensor with the rotation matrix when rotating a first sensor towards a second sensor, and subtracting the result of the multiplying from the readout data produced by the second motion sensor when rotating the first motion sensor towards the second motion sensor.

According to still another aspect, the present invention relates to a method of eliminating passive movement components caused by external forces from readout data produced by at least a first and a second motion sensor when attached to a subject during movement, the readout data including gravitational components, movement components caused by active movement of the subject or subject parts, and the passive movement components, the method comprising estimating a first and second gravitational components produced by the at least first and a second motion sensors, determining a rotation matrix based on the estimated gravitational components, the rotation matrix denoting rotation required for the first sensor to get aligned with the second sensor in orientation, multiplying the readout data produced by the first motion sensor with the rotation matrix when rotating a first sensor towards a second sensor, and subtracting the result of the multiplying from the readout data produced by the second motion sensor when rotating the first motion sensor towards the second motion sensor.

According to yet another aspect, the present invention relates to a computer program product (i.e., a computer-readable medium embodied with a computer program) for instructing a processing unit to execute the method of eliminating passive movement components, as described herein, when the product is run on a computer.

The aspects of the present invention may each be combined with any of the other aspects. These and other aspects of the invention will be apparent from and elucidated with reference to the embodiments described hereinafter.

BRIEF DESCRIPTION OF THE DRAWINGS

Embodiments of the invention will be described, by way of example only, with reference to the drawings, in which.

DESCRIPTION OF EMBODIMENTS

Figure 1:
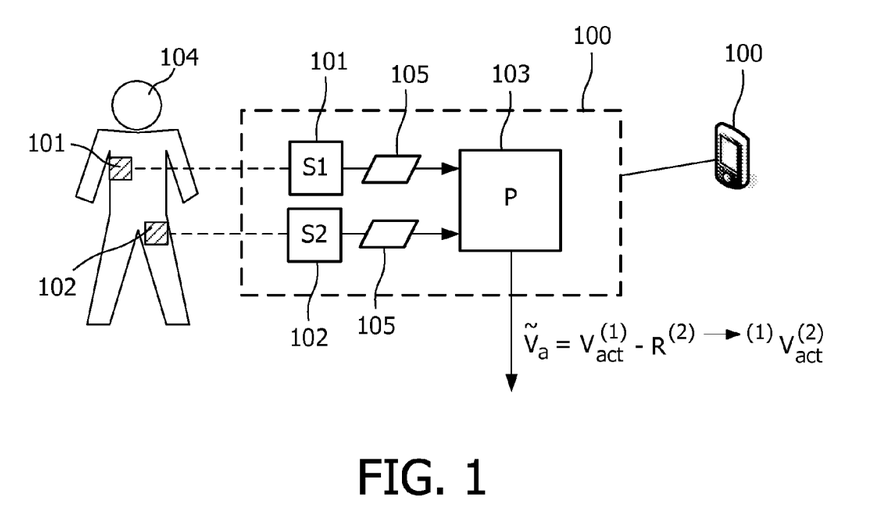
FIG. 1 shows one embodiment of an activity monitoring system according to the present invention.

FIG. 1 shows one embodiment of an activity monitoring system 100 according to the present invention adapted to eliminate passive movement components caused by external forces from readout data 105 produced by at least a first and a second motion sensor when attached to a subject 104 during movement. Preferably, the motion sensors 101, 102 are attached to the subject at different body parts of the subject such that the orientation of the motion sensors coordinate system changes differently when the subject 104 experiences a motion. This will be discussed in more details later in FIGS. 3 and 4. With the term subject is meant a human being, an animal or biological species, and any means that is capable moving at least partly freely in space, such as a robot.

The system comprises at least a first motion sensor 101 and at least a second motion sensor 102, and a processor (P) 103 that is coupled to the motion sensors. In this embodiment, the system is integrated into hand-held device carried by the user, e.g. a mobile phone, PDA, digital watch and the like, where the motion sensors are connected to the processor via a wired or a wireless communication link.

In one embodiment, the motion sensors are tri-axial accelerometers, but other types of sensors are just as well possible such as ultrasonic motion detectors.

Assuming the number of motion sensors is two, e.g. a first and a second tri-axial accelerometer, the readout data 105 may be expressed as:

$$V_a^{(1)} = V_g^{(1)} + V_{act}^{(1)} + V_{pas}^{(1)}, \quad (3)$$

$$V_a^{(2)} = V_g^{(2)} + V_{act}^{(2)} + V_{pas}^{(2)}, \quad (4)$$

where $V_a^{(1)}$ and $V_a^{(2)}$ denote the vectorial acceleration readouts from the two accelerometers, respectively, $V_g^{(1)}$ and $V_g^{(2)}$ are the vectorial gravitational acceleration components, $V_{act}^{(1)}$ and $V_{act}^{(2)}$ are the vectorial acceleration from the active movement, and $V_{pas}^{(1)}$ and $V_{pas}^{(2)}$ the vectorial acceleration from the passive movement. In the cases where active body movements and external motion factors are co-present and none is negligible, both $V_{act}$ and $V_{pas}$ components have significant values in $V_a^{(1)}$ and $V_a^{(2)}$. Direct low-pass or high-pass filtering works only when $V_{act}$ and $V_{pas}$ do not overlap in spectrum, and it is unable to tackle more general cases. By overlap is typically meant the overlap of $V_{act}$ and $V_{pas}$ in frequency, i.e., $V_{act}$ and $V_{pas}$ both have low and/or high frequency components that are not separable in their spectra. This applies for all axes.

It is namely so that when a motion sensor such as a tri-axial accelerometer stays still, it measures the earth gravity that is decomposed along its three sensing axes. If the accelerometer starts to move, besides gravitational acceleration also inertial acceleration is recorded that results from the movement. However, this movement of the accelerometer can be caused by the active movement of the body part to which the sensor is attached as well as the "passive" movement due to external forces. Such passive movements may originate from when the subject is traveling in a vehicle, cycling on a bumpy road, working with a mowing machine, traveling in a train, taking an elevator or escalator, playing in an entertaining park etc. These passive movements may be considered as a "noise" in the acceleration signals in the sense that they form a deviation from the true activity induced acceleration signals caused by the active movement components. It is this passive movement component that the system 100 eliminates.

In practice, the sensing axes of the two accelerometers are normally not aligned. That is to say, in equations (3) and (4), for the gravitational components, $V_g^{(1)} \neq V_g^{(2)}$. Furthermore, the relative orientation of the two sensor coordinate systems changes accordingly with the instant body posture and the activity being conducted (see FIGS. 3 and 4). This implies that the external motion induced accelerations are sensed differently by the two accelerometers, i.e. $V_{pas}^{(1)} \neq V_{pas}^{(2)}$.

The role of the processor 103 is to process the readout data so as to eliminate the passive movement components $V_{pas}^{(1)}$ and $V_{pas}^{(2)}$ caused by external forces. To do so, the gravitational components $V_g^{(1)}$ and $V_g^{(2)}$ are estimated. Let's denote the acceleration vector $V_a^{(1)}$ and $V_a^{(2)}$ for a given moment of time as $V_a^{(1)}[k]$ and $V_a^{(2)}[k]$, where k denotes the sampling moment (in units of e.g. seconds or milliseconds). A temporal estimate for $V_g^{(1)}$ and $V_g^{(2)}$ for the gravitational acceleration vector $V_g$ is determined for a given moment k. In one embodiment, these temporal estimates are determined by the following equations:

$$V_g^{(1)} = V_g^{(1)}[k] = \frac{1}{2K+1} \sum_{m=-K}^{K} V_a^{(1)}[k-m] \quad (5)$$

$$V_g^{(2)} = V_g^{(2)}[k] = \frac{1}{2K+1} \sum_{m=-K}^{K} V_a^{(2)}[k-m] \quad (6)$$

with $V_a^{(1)}[k-m]$ and $V_a^{(2)}[k-m]$ being a sequence of the acceleration readout data from the first and the second motion sensor, respectively, in a discrete time domain, k is the sampling moment, and 2K+1 is the number of samples around $V_a^{(1)}[k]$ and $V_a^{(2)}[k]$ for averaging. As an example, if e.g. the sampling moment is k=3 sec, i.e. the gravitational and the inertial components are to be extracted for $V_a[3\ sec]$ and K=1, then equations (5) and (6) become $$1/(2*1+1)(V_a^{(1)}[2]+V_a^{(1)}[3]+V_a^{(1)}[4]) = V_g^{(1)}[3] = V_g^{(1)}$$
and $$1/(2*1+1)(V_a^{(2)}[2]+V_a^{(2)}[3]+V_a^{(2)}[4]) = V_g^{(2)}[3] = V_g^{(2)},$$

respectively. This is clearly just the average value of the sensor readout over time interval 2-4 seconds. When this time interval is selected reasonable this estimate typically is very good guess because it is unlikely that the inertial forces last very long, but tend to average to something close to zero. As an example, if a person wearing an accelerometer jumps up inertial acceleration vector is initially largest, becomes zero at maximum height (at the instant where the person stops) and becomes negative when the person touches the ground. If the sampling frequency is high enough, the sum of these inertial acceleration vectors over time would be zero, and thus the sum (or the average) of the accelerometer readouts would be equal to the gravitational acceleration. Here it is of course important to select a reasonable time interval to which a reasonable $V_g^{(1,2)}[k]$ is provided. This depends on the application or the implementation of the accelerometer, e.g. the type of sport. If the application is jump, a reasonable time interval could e.g. be 1-2 seconds.

After estimating the first and the second gravitational components produced by the at least first and a second motion sensors, a rotation matrix R is determined based on the estimated gravitational components denoting rotation required for a first sensor to get aligned with a second sensor in orientation, or vice verse, denoting rotation required for the second sensor to get aligned with the first sensor in orientation. Accordingly, it follows that:

$$V_g^{(1)} = R^{(2) \to (1)} V_g^{(2)} \quad (7)$$

$$V_g^{(2)} = R^{(1) \to (2)} V_g^{(1)} \quad (8)$$

where $R^{(2) \to (1)}$ and $R^{(1) \to (2)}$ denote the rotation matrices when rotating $V_g^{(2)}$ towards $V_g^{(1)}$ and when rotating $V_g^{(1)}$ towards $V_g^{(2)}$, respectively.

For tri-axial accelerometers as an example and taking the earth as the reference coordinate system, a rotation matrix R is a 3×3 matrix that may be decomposed into multiplications of three sub-rotation matrices $R_x(\theta)$, $R_y(\phi)$ and $R_z(\psi)$. The three matrices represent a planar rotation of $\theta$ about x-axis, a planar rotation of $\phi$ about y-axis and a planar rotation of $\psi$ about z-axis, respectively, in rotating a vector to another vector. Equation (7) or (8) has maximally three unknowns when $\theta$, $\phi$ and $\psi$ are all non-zero, and therefore it is solvable.

The next step is to multiply the readout data produced by the second motion sensor (equation (4)) with the rotation matrix $R^{(2) \to (1)}$ when rotating the second sensor towards the first sensor. The result is:

$$R^{(2) \to (1)} V_a^{(2)} = V_g^{(1)} + R^{(2) \to (1)} V_{act}^{(2)} + V_{pas}^{(1)}, \quad (9)$$

in which equation (7) and the external motion effect $$R^{(2) \to (1)} V_{pas}^{(2)} \approx V_{pas}^{(1)} \quad (10)$$

are used.

It should be noted that the term first sensor may just as well mean motion sensor producing the readout data in equation (4). Thus, the above mentioned step may just as well indicate that $R^{(1) \to (2)}$ is multiplied with equation (3). Thus, the result would be:

$$R^{(1) \to (2)} V_a^{(1)} = V_g^{(2)} + R^{(1) \to (2)} V_{act}^{(1)} + V_{pas}^{(2)},$$

with $R^{(1) \to (2)} V_{pas}^{(1)} \approx V_{pas}^{(2)}$ and using equation (8).

Finally, subtracting the result of the multiplying, i.e. equation (9) from the readout data produced by the first motion sensor, i.e. subtracting (9) from (3) gives:

$$\tilde{V}_a = V_a^{(1)} - R^{(2) \to (1)} V_a^{(2)} = V_{act}^{(1)} - R^{(2) \to (1)} V_{act}^{(2)}. \quad (11)$$

$\tilde{V}_a$ is used instead of $V_a^{(1)}$ or $V_a^{(2)}$ in predicting physical activity related energy expenditure. It can be seen that $\tilde{V}_a$ relies solely on $V_{act}^{(1)}$ and $V_{act}^{(2)}$ that are induced by true activities, and the impact from external motion factors have been removed. Thus, the output values include only the true activity induced acceleration signals.

Equation (11) basically generates a new vector $\tilde{V}_a$ by linearly combining the two vectors $V_{act}^{(1)}$ and $V_{act}^{(2)}$. As mentioned previously, the motion sensors are preferably attached to the subject at respective positions, such as different body parts of the subject, such that the orientation of the motion sensors coordinate system changes differently when the subject experiences a motion. Therefore, it is ensured that different daily activities induced accelerations, $\tilde{V}_a$, will not approach zero. In fact, the lowest boundary of the magnitude of $\tilde{V}_a$ satisfies $$\|\tilde{V}_a\| \geq \|V_{act}^{(1)}\| - \|R^{(2) \to (1)} V_{act}^{(2)}\|. \quad (12)$$

The 1-norm $\|\|$ gives the sum of the magnitudes of its vector components, i.e., $\|V\|=|x|+|y|+|z|$ for a vector $V=(x, y, z)$, which is the most often adopted norm to come from the accelerometer readout to so-called activity counts. Equation (12) states that the activity counts of $\tilde{V}_a$ will not be smaller than the absolute value of the difference between the activity counts calculated from the two individual sensors. Therefore, $\tilde{V}_a$ is not getting obsolete with this scheme.

The new vector $\tilde{V}_a$ combines the two direct measurements $V_a^{(1)}$ and $V_a^{(2)}$, so the relation with activity related energy expenditure (AEE) or physical activity level (PAL) is expected to be different. Given a certain combination of the sensor wearing positions, the $\tilde{V}_a$-based prediction curve for AEE or PAL can be experimentally obtained and evaluated. There are various manners to achieve this which are out of the scope of this invention disclosure and thus not discussed here.

In implementations, the accelerometers could be integrated in the clothing, e.g., in a garment. For the synchronization of their readouts, the sensors may be real time connected or separately running with or without timestamps. In the latter case, the synchronization is realized with the help of data analysis.

Figure 2:
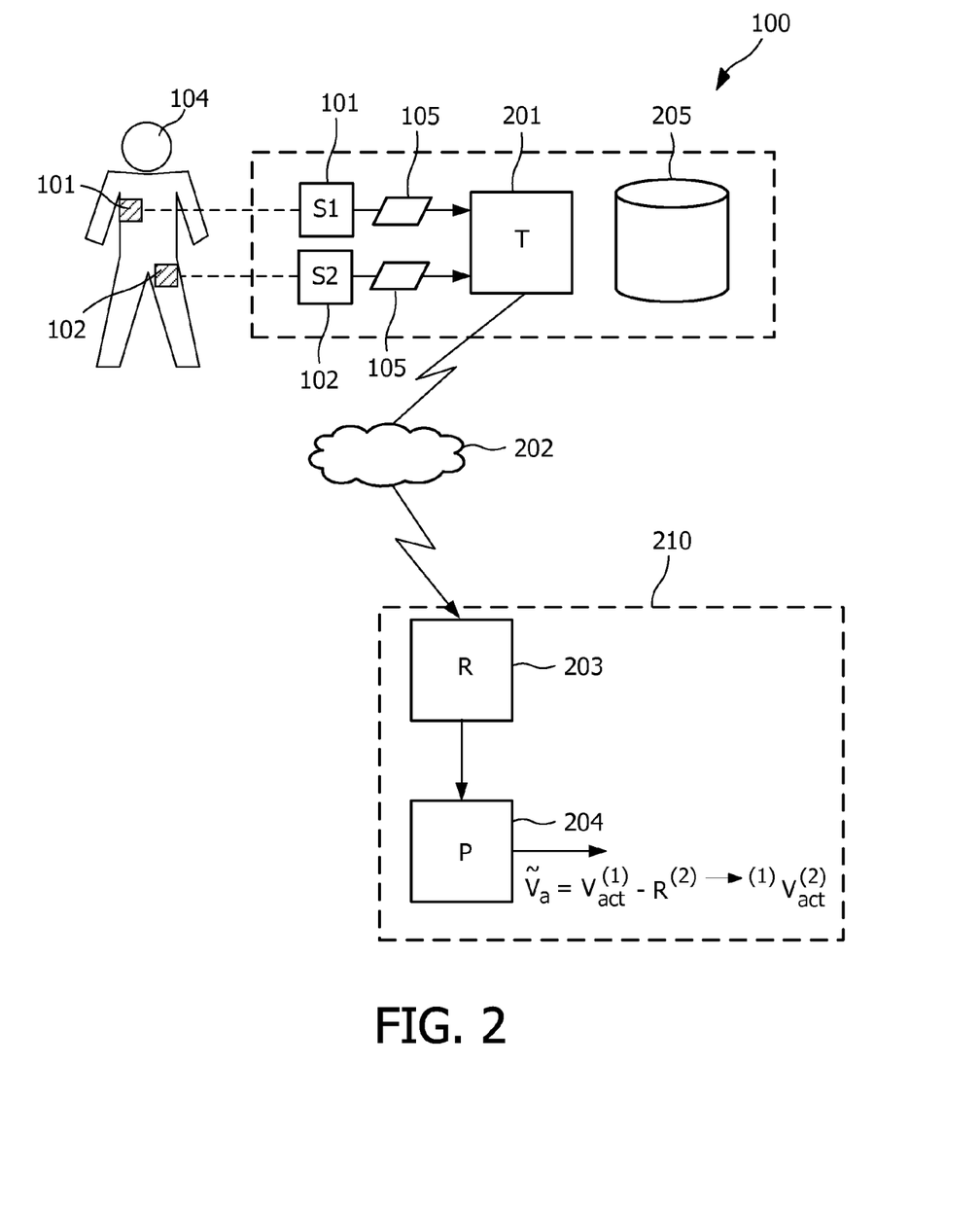
FIG. 2 shows another embodiment of the activity monitoring system in FIG. 1.

FIG. 2 shows another embodiment of the system 100, but it differs from the embodiment in FIG. 1 in that the processing is performed externally from the user 104, e.g. at a clinical center, where the system further comprises a transmitter (T) 201 for transmitting the readout data from the sensors 101, 102 over a communication link 202, e.g. a wired one or a wireless such as the internet, to the external processing station 210. The external processing station 210 comprises a receiver (R) 203, coupled to the processor (P) 204, for receiving the transmitted data 105. The processor (P) 204 then performs the above mentioned processing steps discussed previously in FIG. 1.

This real-time processing scenario is not always needed. In another embodiment, the motion data are first locally stored in a memory 205 of the sensing device e.g. a hand-held device, and later get uploaded to an external computer where data processing takes place. In this case, a transmitter is not required, which makes the battery life of the device longer.

In one embodiment, the motion sensors are three or more and form two or more motion sensor pairs. Generally, only two motion sensors are required arranged at positions that provide significantly different readout signals. However, by using two or more motion sensors it is possible to select out those two which differ most in the readout signals. This could be reflected in higher accuracy, i.e. the more the signal readouts differ, the less chance is that the final readout get obsolete. Accordingly the measurement becomes more stable and accurate.

In another embodiment, the three or more sensors are used so as to form two or more sensor pairs. For each sensor pair, the above mentioned processing steps are performed, thus resulting in two or more equations (11) and thus two or more readouts that are only depending on $V_{act}^{(1)}$ and $V_{act}^{(2)}$. These readouts may then be used to find an average readout value, and in that way the accuracy in the final readout may be increased further.

Figure 3A:
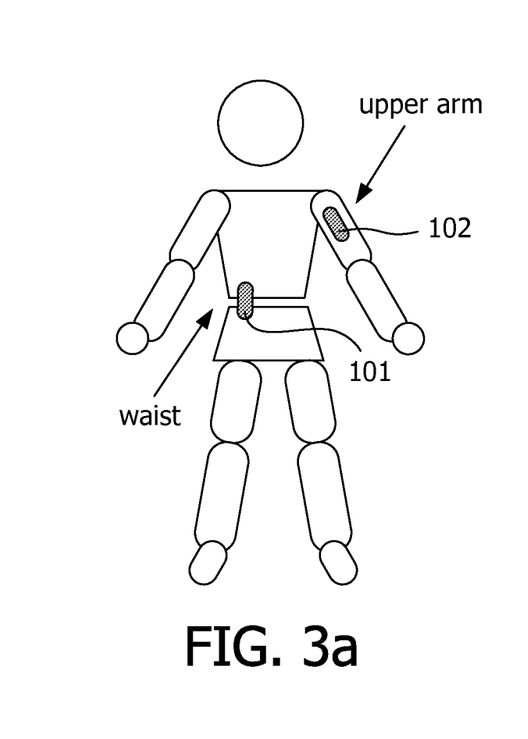
FIG. 3 depicts graphically different combinations of sensor wearing positions.
Figure 3B:
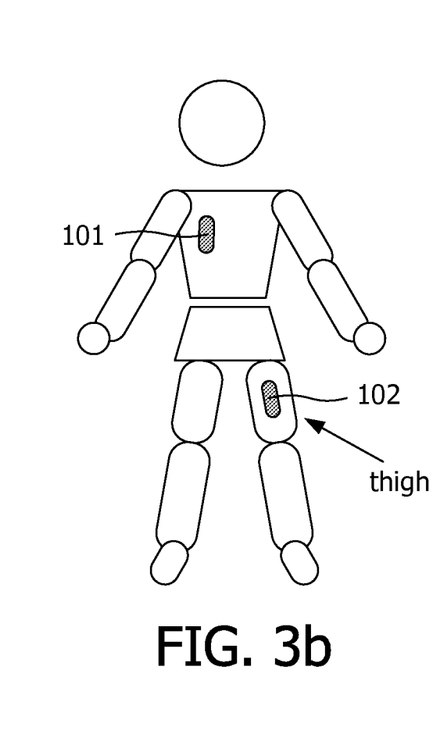
Figure 3C:
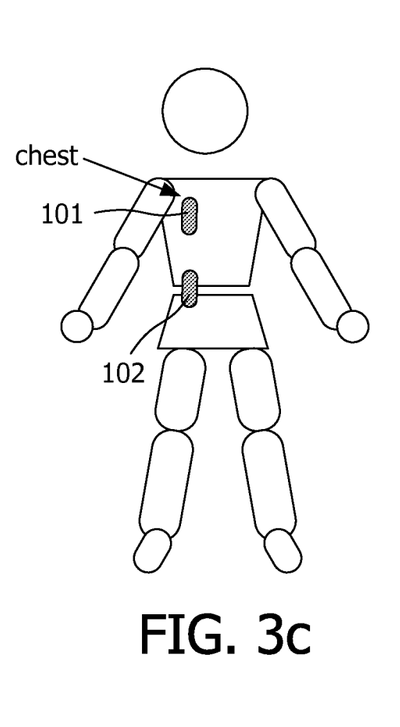

FIG. 3 depicts graphically different combinations of sensor wearing positions in e.g. dual-accelerometer activity monitoring (AM) system. As shown, FIGS. 2a and 2b depict preferred positions for the sensors, whereas the sensor positions depicted in FIG. 2c show unfavourable sensor positions. It is easy to understand that, from the kinematical nature of various body parts during movement, arms behave very differently from waist, whereas in most daily activities chest and waist move as a whole because of the rigidity of the trunk and thus generate very similar accelerations.

Figure 4A:
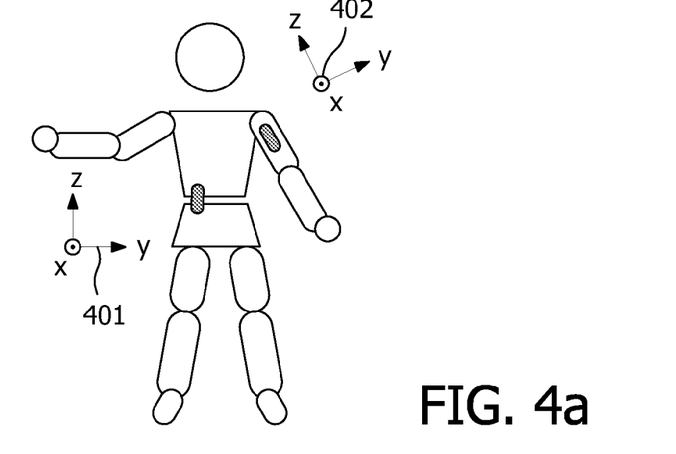
FIG. 4 depicts graphically orientations of sensor coordinate systems in different situations.
Figure 4B:
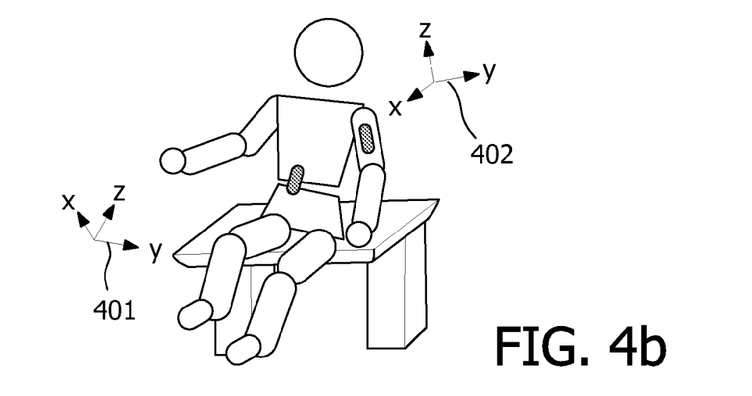
Figure 4C:
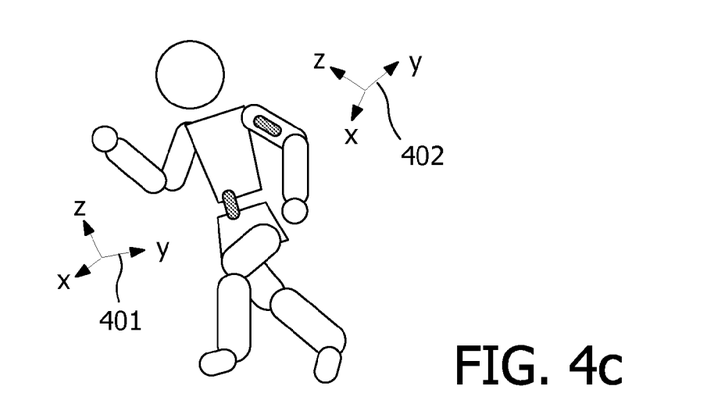

FIG. 4 depicts graphically orientations of sensor coordinate systems 401, 402 in different situations, where FIG. 4a shows the orientation of the sensor during standing posture, FIG. 4b shows the orientation of the sensor during sitting posture, and FIG. 4c shows the orientation of the sensor during running.

Figure 5:
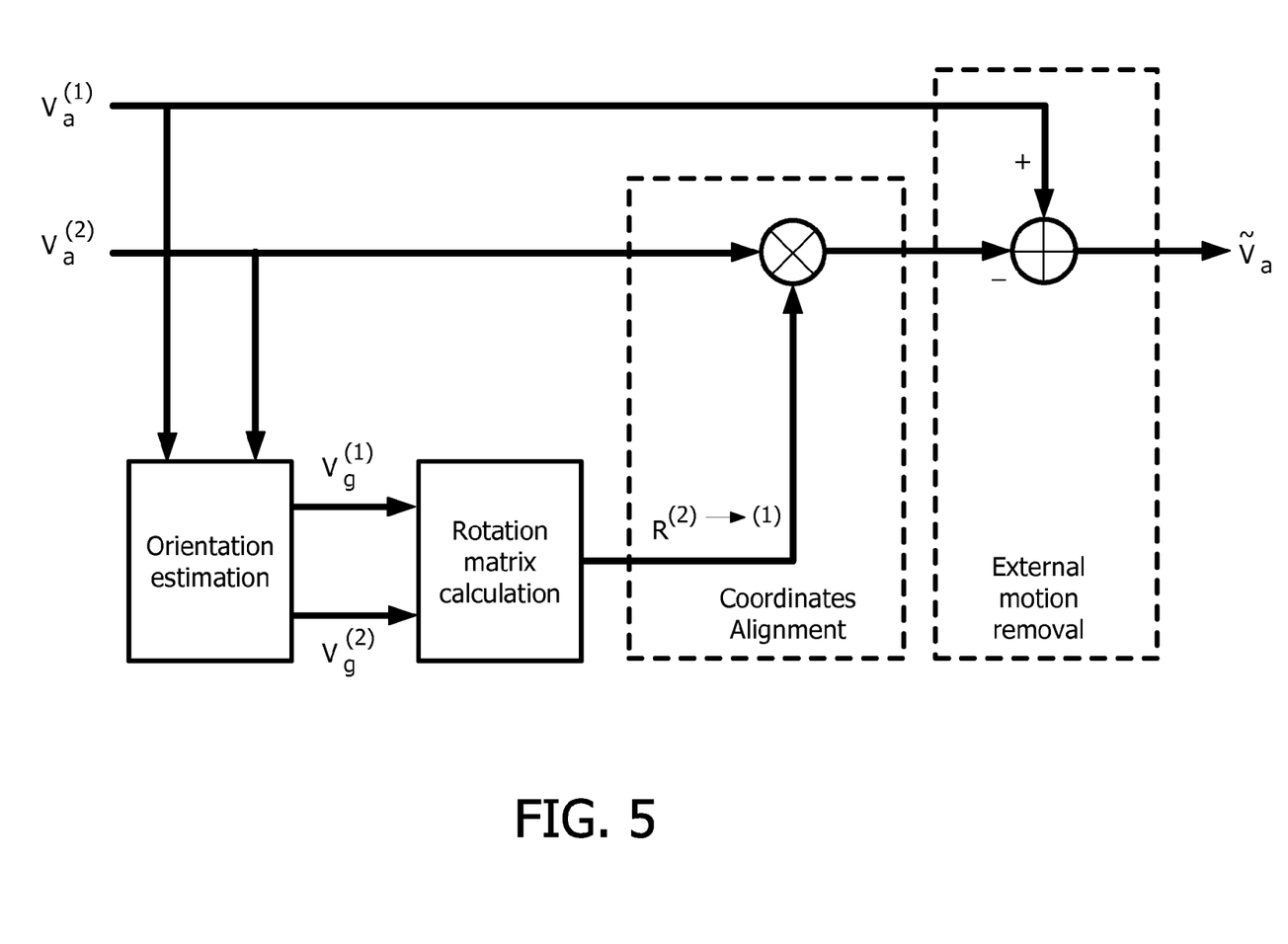
FIG. 5 is a block diagram of the external motion cancellation scheme discussed previously under FIGS. 1 and 2.

FIG. 5 is a block diagram of the external motion cancellation scheme discussed previously under FIG. 1, where the case of rotating $V_g^{(2)}$ towards $V_g^{(1)}$ is chosen as an example, with thick arrows indicating the transferred data of matrix form.

Figure 6:
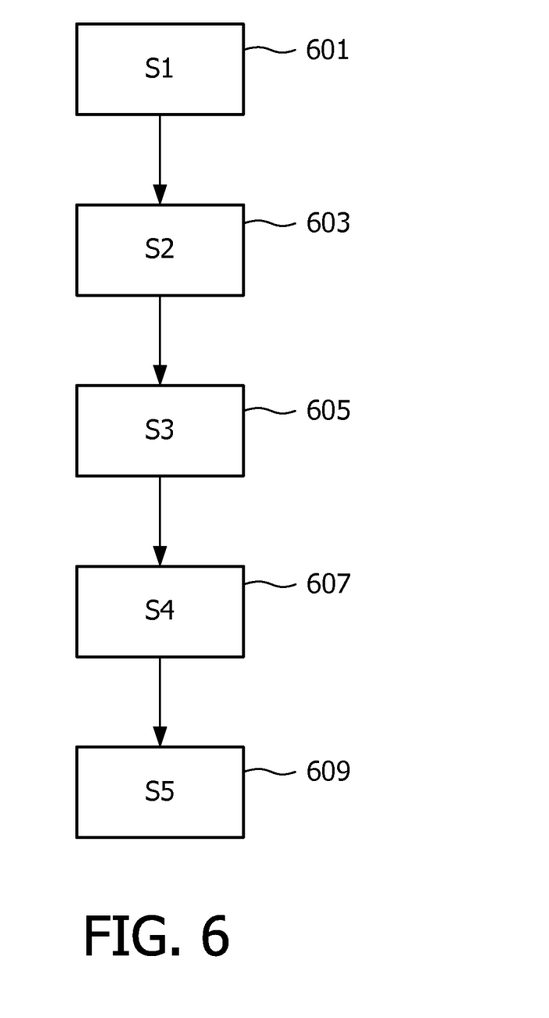
FIG. 6 is a flowchart of a method according to the present invention.

FIG. 6 is a flowchart of a method according to the present invention, for eliminating passive movement components caused by external forces from readout data produced by at least a first and a second motion sensor when attached to a subject during movement. The readout data include, for each respective motion sensor, gravitational component, movement component caused by active movement of the subject or subject parts, and the passive movement component. As mentioned previously, the wearing positions of the motion sensors are chosen such that the orientations of the sensing axes of the motion sensors differ significantly during active movement of the subject, and thus the acceleration readouts will also differ significantly.

In a first step (S1) 601, a first and second gravitational components produced by the at least first and a second motion sensors are estimated, e.g. using equations (5) and (6).

In a second step (S2) 603, a rotation matrix is determined using the estimated gravitational components, where the matrix denotes the rotation required for a first sensor to get aligned with a second sensor in orientation, or vice verse, for the second to get aligned with the first sensor in orientation. Accordingly, this results in that $V_g^{(1)}=R^{(2)\to(1)}V_g^{(2)}$ (Eq. 7) and $V_g^{(2)}=R^{(1)\to(2)}V_g^{(1)}$ (Eq. 8). Also, since the rotation matrix denotes the orientational differences between the two motion sensors, $R^{(2)\to(1)}V_{pas}^{(2)}=V_{pas}^{(1)}$ (Eq. 10) and vice verse, $R^{(1)\to(2)}V_{pas}^{(1)}=V_{pas}^{(2)}$ because of the nature of the external motion effect.

In a third step (S3) 605, the readout data produced by the first motion sensor is multiplied with the rotation matrix when rotating the first sensor towards the second sensor. This may just as well be done vice verse, i.e. by multiplying the readout data produced by the second sensor when rotating the second sensor towards the first sensor. This is shown mathematically in equation (9) where equations (7) and (10) have been inserted.

In a fourth step (S4) 607, the result from step (S3), i.e. equation (9), is subtracted from the readout data produced by the second motion sensor when rotating the first motion sensor towards the second motion sensor, i.e. equation (9) is subtracted from equation (3). The result is thus that the passive movement components get eliminated (see equation (11).

Certain specific details of the disclosed embodiment are set forth for purposes of explanation rather than limitation, so as to provide a clear and thorough understanding of the present invention. However, it should be understood by those skilled in this art, that the present invention might be practiced in other embodiments that do not conform exactly to the details set forth herein, without departing significantly from the spirit and scope of this disclosure. Further, in this context, and for the purposes of brevity and clarity, detailed descriptions of well-known apparatuses, circuits and methodologies have been omitted so as to avoid unnecessary detail and possible confusion.

Reference signs are included in the claims, however the inclusion of the reference signs is only for clarity reasons and should not be construed as limiting the scope of the claims.

The invention claimed is:

1. An activity monitoring system adapted to eliminate passive movement components caused by external forces from readout data produced by at least a first and a second motion sensor when attached to a subject during movement, the readout data including gravitational components, movement components caused by active movement of the subject or subject parts, and the passive movement components, the system comprising:
a processor adapted to:
estimate first and second gravitational components produced by the at least a first and a second motion sensors,
determine a rotation matrix based on the first and second estimated gravitational components, the rotation matrix denoting rotation required for the first motion sensor to get aligned with the second motion sensor in orientation,
multiply the readout data produced by the first motion sensor with the rotation matrix when rotating the first motion sensor towards the second motion sensor to produce a multiplied result, and
subtract the multiplied result from the readout data produced by the second motion sensor when rotating the first motion sensor towards the second motion sensor.

2. The activity monitoring system according to claim 1, where the at least a first and a second motion sensors are attached to the subject at respective positions such that an orientation of a coordinate system of the at least a first and a second motion sensors changes differently when the subject experiences a motion.

3. The activity monitoring system according to claim 2, wherein the respective positions are different body parts of the subject.

4. The activity monitoring system according to claim 1, wherein the at least a first and a second motion sensors comprise three or more motion sensors forming two or more motion sensor pairs, wherein the processor is further adapted to eliminate the passive movement components for each respective motion sensor pair.

5. The activity monitoring system according to claim 1, wherein the at least a first and a second motion sensors comprise three or more motion sensors forming two or more motion sensor pairs, and wherein the processor is further adapted to select one motion sensor pair from the two or more motion sensor pairs as the first and the second motion sensor, the selection being based on monitoring which readout data differ most from the three or more motion sensors.

6. The activity monitoring system according to claim 1, wherein the at least a first and a second motion sensors comprise tri-axial accelerometers.

7. The activity monitoring system according to claim 1, wherein the at least a first and a second motion sensors are integrated into the activity monitoring system and form a hand-held device.

8. The activity monitoring system according to claim 1, further comprising:
a receiver adapted to be coupled to another processor, wherein the at least a first and a second motion sensors are externally located and adapted to transmit the readout data to the receiver.

9. The activity monitoring system according to claim 1, further comprising a memory for storing the readout data produced by at least a first and a second motion sensor.

10. An activity monitoring kit comprising:
a processor, and
at least a first and a second motion sensors adapted to be coupled to the processor, the processor being adapted to eliminate passive movement components caused by external forces from readout data produced by the at least a first and a second motion sensors when attached to a subject during movement, the readout data including gravitational components, movement components caused by active movement of the subject or subject parts, and the passive movement components, wherein eliminating of the passive movement components via the processor comprises:
estimating first and second gravitational components produced by the at least a first and a second motion sensors,
determining a rotation matrix based on the first and second estimated gravitational components, the rotation matrix denoting rotation required for the first motion sensor to get aligned with the second motion sensor in orientation,
multiplying the readout data produced by the first motion sensor with the rotation matrix when rotating a first motion sensor towards a second motion sensor, and
subtracting a result of the multiplying from the readout data produced by the second motion sensor when rotating the first motion sensor towards the second motion sensor.

11. A method of eliminating passive movement components caused by external forces from readout data produced by at least a first and a second motion sensor when attached to a subject during movement, the readout data including gravitational components, movement components caused by active movement of the subject or subject parts, and the passive movement components, the method comprising:
estimating first and second gravitational components produced by the at least a first and a second motion sensors;
determining a rotation matrix based on the estimated gravitational components, the rotation matrix denoting rotation required for the first motion sensor to get aligned with the second motion sensor in orientation;
multiplying the readout data produced by the first motion sensor with the rotation matrix when rotating a first motion sensor towards a second motion sensor; and
subtracting a result of the multiplying from the readout data produced by the second motion sensor when rotating the first motion sensor towards the second motion sensor.

12. A non-transitory computer-readable medium embodied with a computer program of a computer program product for instructing a processing unit to execute the method of eliminating passive movement components according to claim 11 when the product is run on a computer.

* * * * *